(12) United States Patent
Iwai et al.

(10) Patent No.: US 9,714,936 B2
(45) Date of Patent: Jul. 25, 2017

(54) METHOD FOR EVALUATING COSMETIC

(71) Applicant: SHISEIDO COMPANY, LTD., Chuo-ku, Tokyo (JP)

(72) Inventors: Ichiro Iwai, Kanagawa (JP); Eiichiro Yagi, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 14/368,568

(22) PCT Filed: Dec. 20, 2012

(86) PCT No.: PCT/JP2012/083144
§ 371 (c)(1),
(2) Date: Jun. 25, 2014

(87) PCT Pub. No.: WO2013/099775
PCT Pub. Date: Jul. 4, 2013

(65) Prior Publication Data
US 2015/0093772 A1    Apr. 2, 2015

(30) Foreign Application Priority Data

Dec. 26, 2011 (JP) .................. 2011-283045

(51) Int. Cl.
*G01N 33/50* (2006.01)
(52) U.S. Cl.
CPC ..... *G01N 33/5044* (2013.01); *G01N 33/5082* (2013.01); *G01N 2500/10* (2013.01)
(58) Field of Classification Search
None
See application file for complete search history.

(56) References Cited

U.S. PATENT DOCUMENTS

| 2006/0233729 | A1* | 10/2006 | Rose et al. ................. 424/59 |
| 2007/0179198 | A1  | 8/2007  | Iwai et al. |
| 2011/0183018 | A9* | 7/2011  | Maes et al. ................ 424/769 |
| 2011/0262025 | A1* | 10/2011 | Jarrold et al. ............. 382/133 |

FOREIGN PATENT DOCUMENTS

| EP | 1760440 A1    | 3/2007  |
| JP | 10-323184 A   | 12/1998 |
| JP | 2005-249672 A | 9/2005  |
| JP | 2010-223609 A | 10/2010 |
| JP | 2010-271163 A | 12/2010 |

OTHER PUBLICATIONS

Matsumoto, Takeo, "Biomechanical measurement techniques for skin properties," Cosmetic Stage, 2009, 3(5):27-31.
Crowther et al., "Measuring the effects of topical moisturizers on changes in stratum corneum thickness, water gradients and hydration in vivo," British Journal of Dermatology, Jun. 1, 2008, 159:567-577.

* cited by examiner

*Primary Examiner* — Ralph Gitomer
(74) *Attorney, Agent, or Firm* — Foley & Lardner LLP

(57) ABSTRACT

It is an object of the invention to provide a method for evaluating cosmetics that allows development of cosmetics that can contribute to beautiful healthy skin. The object is achieved by a method of evaluating improvement in skin by an applied cosmetic, using as the index the change in stratum corneum thickness during the process of moistening and drying.

3 Claims, 5 Drawing Sheets

US 9,714,936 B2

METHOD FOR EVALUATING COSMETIC

CROSS-REFERENCE TO RELATED APPLICATIONS

This application is a National Stage application of PCT/JP2012/083144, filed Dec. 20, 2012, which claims priority from Japanese application JP 2011-283045, filed Dec. 26, 2011.

BACKGROUND OF THE INVENTION

The present invention relates to a method for evaluating cosmetics. Preferably, the invention relates to a method for evaluating the ameliorating effect on skin, and more preferably the ameliorating effect on the stratum corneum, of cosmetics. The invention still further relates to a method for evaluating cosmetics that is suitable for different environments.

BACKGROUND ART

Skin roughening often occurs in the low-humidity winter season and rarely in the high-humidity summer season, and experience has taught that moisture retention is necessary in order to maintain healthy skin. Furthermore, beautiful skin is considered to be skin that is transparent and has a well-adjusted skin texture, and research is being conducted on methods of evaluating the transparency of the stratum corneum and methods of evaluating drugs that increase stratum corneum transparency (PTLs 1 and 2), and is demonstrating that stratum corneum transparency is associated with the structure of intercellular lipids in the stratum corneum (PTL 3). While it is known that moisture retention is necessary to maintain healthy, moist skin and that transparency is necessary for beautiful skin, the relationship between moisture content of the stratum corneum and skin transparency or health has not been sufficiently studied, and the current state of knowledge is insufficient.

On the other hand, in order to discern the maturity of stratum corneum cells and the state of the skin, methods of measuring the area and thickness of stratum corneum cells, and thereby calculating the platymeric index have also been discovered (PTL 4). However, this publication discloses only measurement of the area and thickness of stratum corneum cells in a normal state (non-moistened state), whereas it involves no measurement of the area of cells swelled with cosmetic water or the like.

CITATION LIST

Patent Literature

[PTL 1] Japanese Unexamined Patent Publication No. 2005-249672
[PTL 2] Japanese Unexamined Patent Publication No. 2010-172200
[PTL 3] Japanese Unexamined Patent Publication No. 2010-175264
[PTL 4] Japanese Unexamined Patent Publication No. 2004-105700

Non-Patent Literature

[NPL 1] Journal of the Japan Cosmetic Science Society Vol. 31, No. 1, pp. 19-24 (2007)

BRIEF SUMMARY OF THE INVENTION

Problems to be Solved by the Invention

There has been a need for clarifying the relationship between the moisture content in the stratum corneum and the healthy and beautiful skin, and for a method for evaluating cosmetic allowing the development of cosmetics that can promote beautiful healthy skin, based on the knowledge. In addition, a formulation have been modified according to the regions in which the cosmetics are to be marketed, and therefore there is a need for a method for evaluating cosmetics comprising a formulation suitable for the environment of the marketed region.

Means for Solving the Problems

As a result of diligent research on the relationship between moisture content of the stratum corneum and the beauty and health of skin, the present inventors have found that the stratum corneum is opaque when moistened with water, and that the transparency increases as it dries (FIG. 1), while the stratum corneum moistened with water exhibits a low skin barrier function, and the skin barrier function increases as it dries (FIG. 2). Since the transparency and skin barrier function of the stratum corneum contributes to beautiful skin and healthy skin, respectively, these experimental results indicated that for beautiful healthy skin, the dry state is more essential than the moist state. Since it has traditionally been considered that moisture retention is important for beautiful healthy skin and that a dry state should be avoided, this was a surprising observation.

When a research for investigating the causes of increased transparency and skin barrier function as the moisture content of the stratum corneum decreases were carried out, it was found that decreasing moisture content of the stratum corneum is associated with orderly structuralization of the keratin structure of the stratum corneum, as well as orderly structuralization of intercellular lipids composed of ceramide, cholesterol, fatty acids and the like, thereby causing stabilization of the lamellar structure, and providing with a barrier function (FIG. 3).

The present inventors induced water swelling of stratum corneum with impaired transparency and skin barrier function, wherein the stratum corneum is subjected to freeze-drying, thereby resulting in disintegration of the keratin structure and lamellar structure, subsequently subjected it to an ordinary drying process, and then found that the transparency and skin barrier function were restored by the process (FIGS. 4 and 5). It was interpreted that swelling of the stratum corneum with water destabilized the keratin structure and lamellar structure, and that the keratin structure and lamellar structure were reconstituted in an orderly manner during the drying process.

Based on this knowledge, the present inventors reached the conclusion that in the process of skin care for obtaining beautiful healthy skin, instead of simply moistening as has been done in the past, it is important to first bring the stratum corneum to a moist state, sufficiently swell it to destabilize the keratin structure and lamellar structure, and then dry it to reconstitute the keratin structure and lamellar structure, and succeeded in inventing a method for evaluating whether or not a cosmetic has such an effect.

More specifically, the present inventors found that when a liquid having an effect of improving transparency of the stratum corneum is used in the process of moisturizing and then drying the stratum corneum, the thickness of the stratum corneum cells changes and the change rate in the thickness of the stratum corneum increases despite little change in the area of the stratum corneum cells, whereas if a liquid that does not improve transparency of the stratum corneum is used, there is virtually no change in the thickness and area of the stratum corneum cells (FIGS. 6 and 7). The change rate of the thickness of the stratum corneum is an index represented by the following formula:

Change Rate of the thickness of the Stratum corneum (%)=$(B-A)\times 100/A - (C-B)\times 100/C$, wherein A is the thickness of the stratum corneum before moistening, B is the thickness of the stratum corneum after moistening, and C is the thickness of the stratum corneum after drying. Based on this knowledge, the present inventors accomplished an invention relating to a method of evaluating the skin-ameliorating property of an applied cosmetic, using the thickness of stratum corneum selected from the group consisting of skin stratum corneum, isolated stratum corneum, and a cultured stratum corneum sheet in a moist state and after drying, as the index. Specifically, the present invention relates to the following inventions.

(1) A method for evaluating cosmetics, using as the index the change in thickness of the stratum corneum during moisturing and then drying the stratum corneum.

(2) The evaluation method according to (1), wherein the change in thickness of the stratum corneum during moisturing and then drying the stratum corneum uses the change rate of thickness of the stratum corneum as the index, the evaluation method comprising the following steps:

measuring the thickness (A) of cells or a cell layer of stratum corneum selected from the group consisting of skin stratum corneum, isolated stratum corneum and a cultured stratum corneum sheet before applying cosmetics;

measuring the thickness (B) of cells or a cell layer in the moist state;

measuring the thickness (C) of cells or a cell layer in the dry state; and calculating the change rate of thickness of the stratum corneum during the process of moisturizing, and then drying the stratum corneum based on Formula 1:

the change rate of thickness of Stratum corneum= $(B-A)\times 100/A - (C-B)\times 100/C$.  Formula 1)

(3) The method according to (1) or (2), further comprising a step of judging that the cosmetic has an ameliorating effect on skin if the change rate of thickness of the stratum corneum is 20% to 150%.

(4) The method according to any one of (1) to (3), further comprising a step of judging that the cosmetic has an ameliorating effect on skin if the change rate of thickness of the stratum corneum is 25% to 100%.

(5) The method according to any one of (1) to (4), wherein the ameliorating effect on skin is an ameliorating effect on the stratum corneum.

(6) The method according to (5) above, wherein the ameliorating effect on the stratum corneum is an ameliorating effect on stratum corneum transparency.

As a result of further careful research on the drying step, the present inventors found that stratum corneum transparency and skin barrier function vary depending on changes in the humidity during the drying step (FIG. 8 and FIG. 9). Specifically, it was found that when stratum corneum swelled with water has been dried under high humidity, both the transparency and skin barrier function of the stratum corneum are superior compared to those dried under low humidity. This is believed to be due to the slow evaporation of water under high humidity, which results in orderly reconstitution of the keratin structure and lamellar structure. Consequently, adjusting the components in cosmetic water to control the rate of the drying step allows evaluation of whether the cosmetic is suitable for the environment, such as the climate in which it is to be used (that is, the standard temperature and standard humidity of the marketed region). The present inventors thereupon developed the following inventions.

(6) A method for evaluating cosmetics suitable for a given environment, comprising:

applying cosmetics onto stratum corneum selected from the group consisting of skin stratum corneum, isolated stratum corneum and a cultured stratum corneum sheet (not including melanin);

drying the cosmetics at a prescribed temperature and a prescribed humidity;

measuring the moisture content (%) and stratum corneum transmittance (%) during the drying step, thereby creating a plot diagram and obtaining a fitted curve;

judging whether or not the fitted curve obtained in the previous step is within a range between a fitted curve (1) obtained in a step of applying water to the stratum corneum and drying under conditions of the prescribed temperature and the humidity ranged from 30% to 90%, and a fitted curve (2) obtained in a step of drying under conditions of the prescribed temperature and 90% humidity; and evaluating that the cosmetic is suitable for the environment if the fitted curve is contained within the range.

(7) The evaluation method of (6), wherein the lower limit of humidity under the condition to obtain the fitted curve (1) is selected from the group consisting of 60%, 70%, and 80%.

(8) A method for evaluating cosmetics that are suitable for a given environment, the method comprising:

applying cosmetics onto stratum corneum selected from the group consisting of skin stratum corneum, isolated stratum corneum and a cultured stratum corneum sheet (not including melanine);

drying the cosmetic at a prescribed temperature and a prescribed humidity;

measuring the stratum corneum transmittance after drying; and evaluating that the cosmetic is suitable for the environment if the stratum corneum transmittance is 85% to 100%.

Effect of the Invention

The present inventors have found that changes in the thickness of the stratum corneum during the process of moistening and drying relate to the transparency of the stratum corneum after the process of moistening and drying. According to the invention, therefore, using the thickness of the stratum corneum during the process of moistening and drying as an index allows judgment of whether or not a liquid used is effective in terms of its ameliorating effect on skin, and is useful for primary screening during product development. According to another mode of the invention, the suitability of a cosmetic for a given environment is judged, thereby facilitating product development.

DETAILED DESCRIPTION OF THE INVENTION

Description of Embodiment of the Invention

Figure 1:
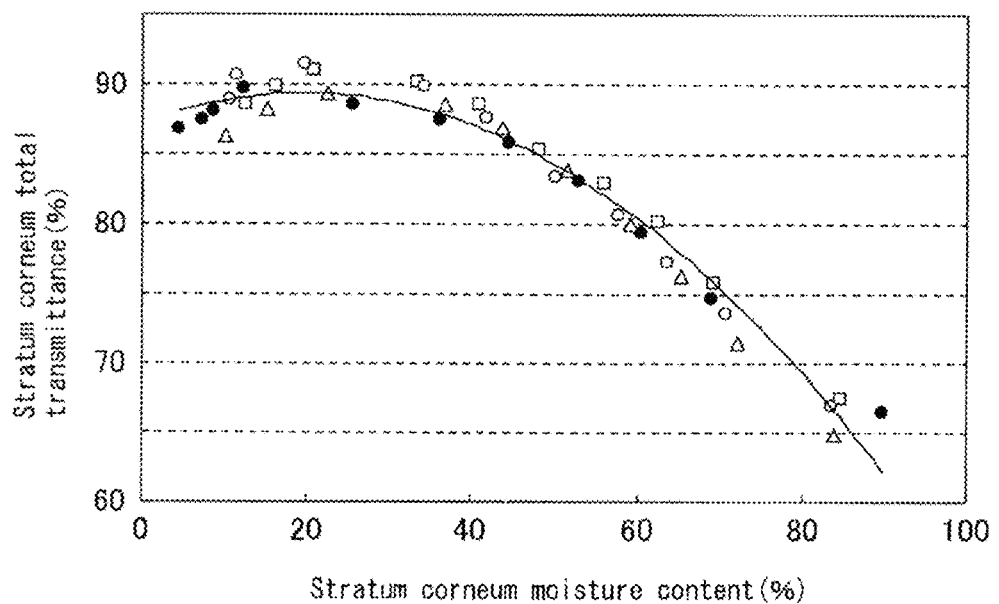
FIG. 1 is a graph showing the relationship between stratum corneum moisture content and stratum corneum total transmittance.

According to a first aspect, the present invention provides with a method for evaluating cosmetics using as the index the change rate in thickness of the stratum corneum during the process of moistening and drying the stratum corneum. This evaluation method enables to evaluate cosmetics for the stratum corneum transparency ameliorating effect, stratum corneum ameliorating effect, and further the skin ameliorating effect and skin beautifying effect of the cosmetics, and thereby to carry out screening for cosmetics that are useful for these effects.

A "moist state" in the present invention is an equilibrium state in which a cosmetic has been applied so as to sufficiently moisten the stratum corneum, with the cosmetic sufficiently penetrating the stratum corneum. The time to reach a moist state differs according to the type of cosmetic and therefore the time required to reach a moist state cannot be defined for all cases, but a moist state may be considered to have been reached if the cosmetic is maintained so as not to dry for at least 1 minute, preferably at least 5 minutes, more preferably at least 10 minutes and even more preferably at least 30 minutes after application of the cosmetic. Since it is sufficient to reach an equilibrium state, it usually causes no problem if the cosmetic application time is longer than this time.

Change rate in the thickness of the stratum corneum in the present invention is change rate during the process of applying and drying the cosmetic, and is defined by the following formula 1):

$$\text{Stratum corneum thickness change rate }(\%) = (B-A) \times 100/A - (C-B) \times 100/C, \qquad \text{Formula 1)}$$

wherein, A is the thickness of cells or a cell layer of stratum corneum selected from the group consisting of skin stratum corneum, isolated stratum corneum and a cultured stratum corneum sheet, B is the thickness of cells or a cell layer of the stratum corneum in a moist state after application of the cosmetic, and C is the thickness of the cells or a cell layer of the stratum corneum after drying. Thus, the method for evaluating cosmetics according to the invention preferably comprises the following steps:

a step of measuring the thickness (A) of cells or a cell layer of stratum corneum selected from the group consisting of skin stratum corneum, isolated stratum corneum and a cultured stratum corneum sheet before application of a cosmetic;

a step of measuring the thickness (B) of cells or a cell layer in the moist state;

a step of measuring the thickness (C) of cells or a cell layer in the dry state; and a step of calculating the thickness change rate of the stratum corneum during the process of moisturing and drying the stratum corneum, by means of formula 1). According to the invention, an ameliorating effect on skin is considered to have been obtained if the thickness change rate of the stratum corneum exceeds 20%. More preferably, if the lower limit for the range for the thickness change rate of the stratum corneum is selected from the group consisting of 20%, 25%, 30% and 40%, and while the upper limit is not particularly restricted, although from the viewpoint of the swelling limit, it is selected from the group consisting of 100%, 120%, 150% and 200%, an ameliorating effect on skin is considered to have been obtained.

"stratum corneum" in the present invention includes all of in vivo stratum corneum itself, a preparation from the in vivo skin, and stratum corneum obtained from cell culture, such as skin stratum corneum, isolated stratum corneum and cultured stratum corneum sheets.

"Skin stratum corneum" refers specifically to the stratum corneum in human skin, and when the term "skin stratum corneum" is used for the purpose of the present invention it relates to an in vivo method in which the cosmetic is directly applied onto the stratum corneum of the skin of an organism. The location of the skin may be any site or region of the body, such as the cheek, chin, back of the hand or trunk.

The "isolated stratum corneum" may be obtained by an invasive method such as surgical means, but in the purpose of evaluating a cosmetic, preferably it is obtained from skin by a noninvasive method, for ease or for ethical reasons. Noninvasive methods include tape stripping and scrubbing methods that are commonly employed in the technical field (NPL 1). Tape stripping can be accomplished by attaching an adhesive tape strip or a Post-It (product of Sumitomo-3M) to the skin surface layer and peeling it off to detach the skin stratum corneum directly onto the adhesive tape, and this is especially preferred for the purpose of the invention.

A preferred tape stripping method is one in which the skin surface is first covered with an adhesive tape strip or Post-It cut to a suitable size (for example, 5×5 cm) lightly placed over the skin surface, and force is applied equally on the entire tape to flatten it, after which the adhesive tape is peeled off with a uniform force. The adhesive tape used may be commercially available cellophane tape, and for example, it may be Scotch Superstrength Mailing Tape (3M) or the like. Also, the Post-It used may be Post-It cover-up tape or the like by Sumitomo-3M.

A cultured stratum corneum sheet is a sheet of stratum corneum obtained by in vitro culturing, and includes stratum corneum sheets isolated from cultured and maintained skin tissue harvested from human or experimental animal skin, and stratum corneum sheets obtained from three-dimensionally cultured skin obtained by culturing fibroblasts, or fibroblasts differentiated in vitro from stem cells (for example, epithelial stem cells, embryonic stem cells or induced pluripotent stem cells), on a culture support composed of a polymer such as collagen, fibrin or polylactic acid, or a polysaccharide such as chitin, chitosan, chondroitin sulfate or hyaluronic acid. The stratum corneum sheet is isolated from culture-supported skin tissue using a method such as treatment with a protease in physiological saline having controlled calcium ion and magnesium ion concentrations. Three-dimensionally cultured skin used may be a human three-dimensional cultured epidermal model product commercially available from LabCyte EPI-MODEL (Japan Tissue Engineering).

According to another aspect of the invention, the invention relates to a method for evaluating the usage of a cosmetic based on the index the thickness change of the stratum corneum. Specifically, the method for evaluating the method of the usage of a cosmetic comprises the following steps:

a step of measuring the thickness (A) of cells or a cell layer of stratum corneum selected from the group consisting of skin stratum corneum, isolated stratum corneum and a cultured stratum corneum sheet before application of a cosmetic;

a step of measuring the thickness (B) of cells or a cell layer in the moist state;

a step of measuring the thickness (C) of cells or a cell layer in the dry state; and a step of calculating the thickness change rate of the stratum corneum during the process of drying after the stratum corneum has been moistened, by the following formula 1:

$$\text{Stratum corneum thickness change (\%)} = (B-A) \times 100 / A - (C-B) \times 100 / C. \quad \text{Formula 1}$$

According to the invention, an ameliorating effect on skin is obtained by use of the cosmetic if the thickness change of the stratum corneum exceeds 20%. More preferably, use of the cosmetic may be judged suitable when the stratum corneum thickness change rate is greater than 20%, greater than 25%, greater than 30%, greater than 40% or greater than 50%. There are no particular restrictions on the upper limit, but from the viewpoint of the swelling limit, it is preferably selected from among less than 100%, less than 120%, less than 150% and less than 200%. Methods for evaluating methods of using cosmetics, where the cosmetics are applied to skin stratum corneum, are employed in beauty parlors, cosmetic shops and aesthetic salons.

The thickness of the stratum corneum is generally the thickness of the cell layer of the stratum corneum, but from the viewpoint of measuring the change rate in the thickness of the stratum corneum, the change rate in the thickness of the stratum corneum may be measured by comparing not only the thickness of the stratum corneum cell layer but also the thickness of one cell in the stratum corneum. The thickness of the stratum corneum can be measured using any desired method that has been conventionally used, such as one using a fluorescent microscope or atomic force microscope (PTL 4 and NPL 1). There may alternatively be used a multiphoton scanning laser microscope or confocal biomicroscope, or the like. More specifically, when the cell thickness of the isolated stratum corneum is to be measured, a fluorescent microscope or atomic force microscope may be used to measure the length from cell membrane to cell membrane in the thickness direction of the flat-shaped stratum corneum cells, thereby allowing measurement of the thickness of the cells in the isolated stratum corneum. Similarly, the thickness of the stratum corneum cell layer can be measured as the thickness of the isolated stratum corneum cell layer, by measuring the length from the cell membranes of the lowermost layer cells of the stratum corneum cells layered in the isolated stratum corneum, to the cell membranes of the uppermost layer cells.

According to the invention, "cosmetic" refers to a cosmetic to be applied to skin, such as cosmetic water, latex, essence, cream, foundation or the like, but there is no limitation to these. It includes all substances that are not directly for the purpose of improving skin but are to be applied onto skin, and for example, it includes sunscreens, insect repellents, allopecia agents and hair restorers.

Yet another aspect of the invention relates to a method for evaluating cosmetics suitable for a given environment. Specifically, it relates to a method for evaluating cosmetics that are suitable for a given environment, the method comprising:

(1) a step of applying a cosmetic onto stratum corneum selected from the group consisting of skin stratum corneum, isolated stratum corneum and a cultured stratum corneum sheet;

(2) a step of drying the cosmetic at a prescribed temperature and a prescribed humidity;

(3) a step of measuring the moisture content (%) and stratum corneum transmittance (%) in the drying step, thereby creating a plot diagram and obtaining a fitted curve;

(4) a step of judging whether or not the fitted curve obtained in the previous step is within a range between a fitted curve obtained in a step of applying water to stratum corneum selected from the group consisting of skin stratum corneum, isolated stratum corneum and cultured stratum corneum sheet (not containing melanin) and drying under conditions of the prescribed temperature and at least 30% and less than 90% humidity, and preferably at least 60% and less than 90% humidity, and a fitted curve obtained in a step of drying under conditions of the prescribed temperature and 90% humidity; and (5) a step of evaluating that the cosmetic is suitable for the prescribed environment if the fitted curve is contained within the range.

Since there was no significant difference in skin barrier function between drying in 60% humidity and drying in 90% humidity (FIG. 9), a cosmetic can be evaluated to be suitable for a particular environment even when the method includes, instead of steps (4) and (5), a step of evaluating whether the cosmetic is suitable for the particular environment if the stratum corneum total transmittance is higher than 85%, which corresponds to the stratum corneum total transmittance at the end point of drying when drying has been under conditions of the prescribed temperature and 60% humidity. In this case, the stratum corneum transmittance is preferably higher than 90%.

The rate of drying of the cosmetic may vary depending on the amount and concentration of the components it contains. The components in the cosmetic may include water or alcohols such as ethanol, glycerin or polyethylene glycol as bases, amino acids such as glycine, betaine, Na pyrrolidone carboxylate or saccharides such as fructose, maltitol, mannitol or trehalose, as humectants, hyaluronic acid, collagen, ceramide or the like as active ingredients, sodium citrate, citric acid or sodium lactate as diluting agents, and benzoic acid salts or sorbic acid as antiseptic agents, with no particular limitation to these. Of these, the volatile components increase the drying speed while the solutes, and especially the hydrophilic substances such as polymers including polyethylene glycol, lower the drying speed, and therefore selection of these components and their amounts alter the drying speed of the cosmetic obtained by formulation. The invention allows evaluation of whether or not the cosmetic obtained by formulating these components is suitable for the environment of the region in which it is to be marketed.

According to the invention, the environment of a marketing region is the environment in the region in which the cosmetic is to be marketed, and for example, ii refers to the climate, and particularly the temperature and humidity, which also varies widely depending on the season of the marketing region. Thus, according to a more preferred embodiment of the invention, it is possible to evaluate whether a cosmetic is suited for different seasons in the marketing region, for example, for the dry season or rainy season, or for the spring, summer, fall or winter seasons.

According to the invention, the skin barrier function is evaluated by transepidermal water loss (TEWL). The TEWL is the amount of transpiration of moisture through the stratum corneum, a lower TEWL indicating higher stratum corneum skin barrier function and higher TEWL indicating lower stratum corneum skin barrier function. The relationship between skin barrier function and skin roughening is described in PTL 2.

Concrete examples will now be provided for a more detailed explanation of the invention. However, the invention is in no way limited by the examples.

EXAMPLES

Example 1: Evaluation of Stratum Corneum Transparency in Relation to Stratum Corneum Moisture Content (Preparation of Stratum Corneum Sample)

A three-dimensional human epidermis culture model (LabCyte EPI-MODEL, Japan Tissue Engineering) in a 12-well plate was incubated for 30 minutes at 37° C. in 0.1% trypsin solution/isotonic phosphate buffer to prepare a stratum corneum sheet with a diameter of approximately 10 mm. Each stratum corneum sheet was dried at a temperature of 34° C. using an MTH-2200 Thermo-Hygrostat (Sanyo Electric Co., Ltd.), to obtain stratum corneum sheets with different stratum corneum moisture contents.

(Method of Measuring Stratum Corneum Moisture Content)

The wet weight of the stratum corneum whose moisture content is of interest is measured with a Mettler or the like. The static electricity is removed if necessary with an Ionizer (STABLO, Shimadzu Corp., Nagoya, Japan). The weight measurement is conducted every second for 1 minute, and the average value is recorded. The absolute dry weight of the stratum corneum is then measured. Specifically, the stratum corneum is heated at 120 degrees for 2 hours to remove most of the moisture. Next, it is brought to an absolute dry condition with a moisture adsorption/desorption apparatus (IGAsorp, Hiden Isochema Ltd., WA, UK) while circulating a 0% humidity nitrogen gas stream for 2 hours, and the stratum corneum absolute dry weight at 0% humidity is measured with the moisture adsorption/desorption apparatus. The stratum corneum moisture content was calculated based on the following formula.

Stratum corneum moisture content (%)=[(stratum corneum wet weight−stratum corneum absolute dry weight)/(stratum corneum wet weight)]×100

(Measurement of Stratum Corneum Total Transmittance)

The transparency measuring apparatus of the invention comprises a white light source as a standard light source of C rating according to the CIE (Commission Internationale de l'Eclairage), a holding fixture for the stratum corneum sample, a screen as a shielding for light that does not pass through the stratum corneum sample, an integrating sphere that homogenizes light that has passed through the stratum corneum sample, and a photometer that measures the intensity of light guided from the integrating sphere. After measurement of the stratum corneum moisture content, the stratum corneum sheet is mounted on a transparency measuring apparatus according to the invention and irradiated with white light from the light source, the light passing through the stratum corneum sheet being directed to the integrating sphere, and the homogenized light intensity was measured. The results for the measured value of the total transmittance, i.e. the intensity of light that has passed through the stratum corneum sheet, was expressed as a percentage, divided by the measured value for the intensity of white light guided directly from the light source to the integrating sphere, in a blank state without mounting of the stratum corneum sheet (FIG. 1).

Example 2: Evaluation of Skin Barrier Function of Stratum Corneum in Relation to Stratum Corneum Moisture Content (Measurement of Moisture Transpiration from Stratum Corneum)

Figure 2:
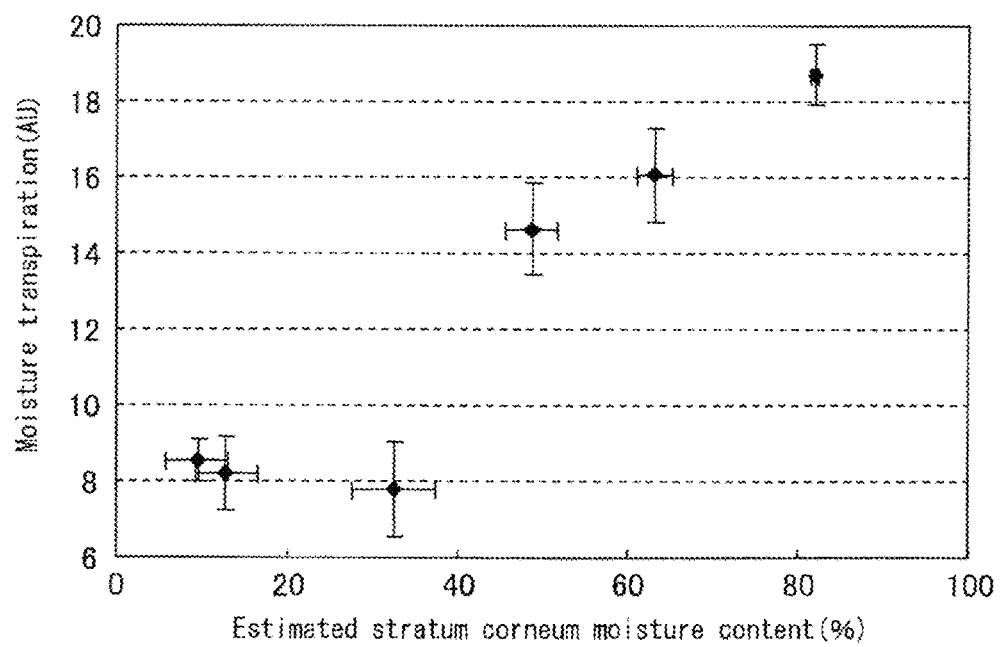
FIG. 2 is a graph showing the relationship between stratum corneum moisture content and moisture transpiration, demonstrating that skin barrier function of the stratum corneum increases as stratum corneum moisture content decreases.
Figure 3:
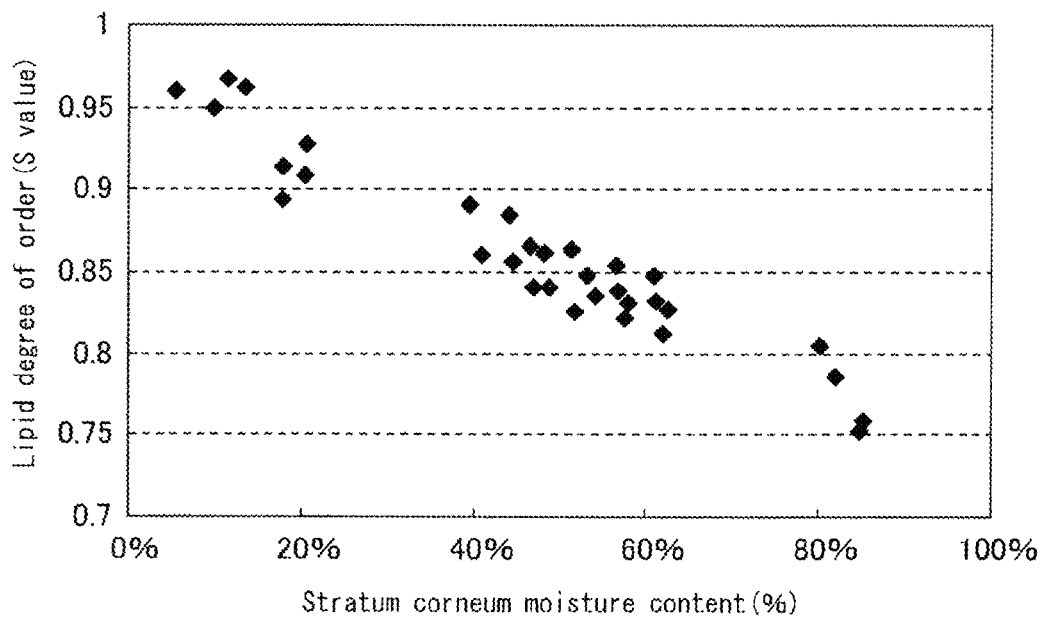
FIG. 3 is a graph showing the relationship between stratum corneum moisture content and lipid degree of order.

The dried stratum corneum sheet was mounted on a Franz cell (PermeGear, Inc., U.S.). The receiver side of the stratum corneum sheet was soaked with water while the donor side was kept empty, thereby exposing the upper side of the stratum corneum sheet to a gas phase and the lower side to a liquid phase, with the stratum corneum sheet situated on the gas-liquid interface. Two hours after stabilization of moisture transpiration from the stratum corneum, a VapoMeter (Delfin Technologies Ltd., Finland) was used to measure the moisture transpiration in nail mode (FIG. 2).

Example 3: Evaluation of Lipid Order of Stratum Corneum in Relation to Stratum Corneum Moisture Content (Preparation of Stratum Corneum Sample)

A three-dimensional human epidermis culture model (LabCyte EPI-MODEL, Japan Tissue Engineering) in a 12-well plate was incubated for 30 minutes at 37° C. in 0.1% trypsin solution/isotonic phosphate buffer to prepare a stratum corneum sheet with a diameter of approximately 10 mm.

(Reaction with 5DSA)

The stratum corneum sheet was attached to a glass plate (8 mm×70 mm×0.5 mm) and treated with 50 mL of 0.001% 5-doxylstearic acid (5-DSA; product of Aldrich) as a spin probe, reacted at 37° C. for 1 hour and then rinsed with water.

(ESR Measurement)

An MTH-2200 was used for incubation of the stratum corneum sheet at 34° C., 60% humidity, and ESR measurement was performed at 0 hours, 30 minutes, 1 hour, 1.5 hours, 2 hours, 2.5 hours, 3 hours, 5 hours and 18 hours from the start of incubation. The measurement was conducted at room temperature using an X-band ESR apparatus (JES-REIX, product of JEOL Corp.). Data analysis was performed to determine the degree of order S by the conventionally used geometric method.

The measuring conditions were as follows. Microwave output: 10 mW, field modulation width: 0.2 mT, time constant: 1 second, sweep time: 8 minutes.

Based on the results of Example 1 and Example 2, an increase in transparency and skin barrier function of the stratum corneum was exhibited with decreasing the stratum corneum moisture content. Also, based on the results of Example 3, the degree of order of intercellular lipids was improved as the stratum corneum moisture content decreased. This is because structuralization of the lipids as drying progressed resulted in increased stratum corneum stability. This demonstrates that reduction from a sufficiently moistened state to a suitable stratum corneum moisture content is necessary for skin having high transparency (beauty) and a high skin barrier function (healthy skin).

Figure 4:
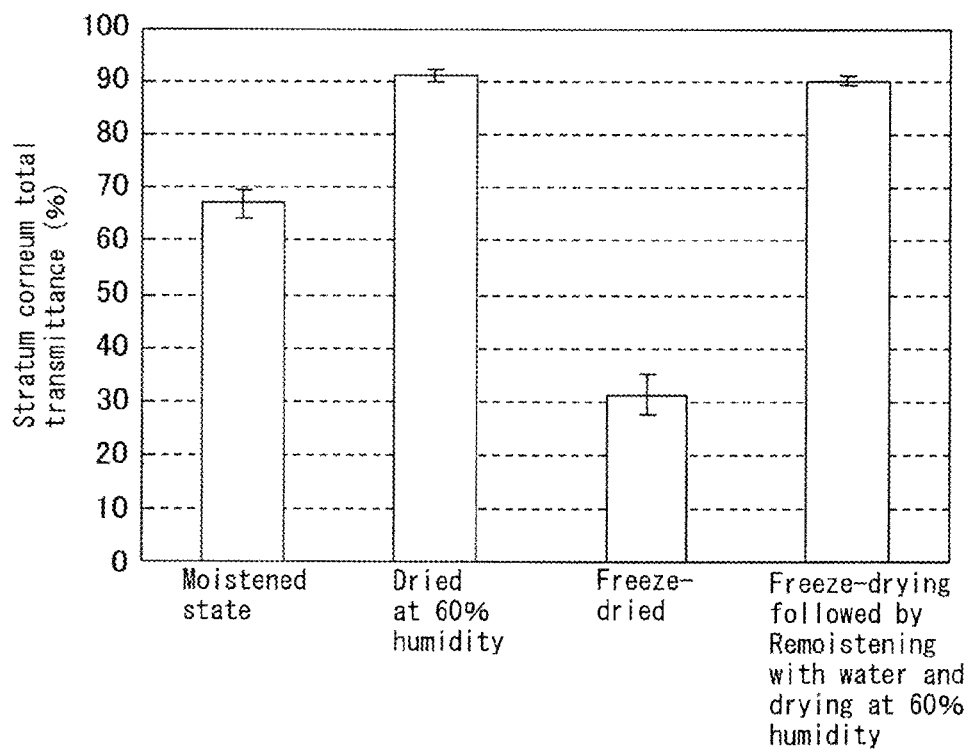
FIG. 4 is a graph showing improvement in stratum corneum transparency when the stratum corneum roughened by freeze-drying is remoistened with water.
Figure 5:
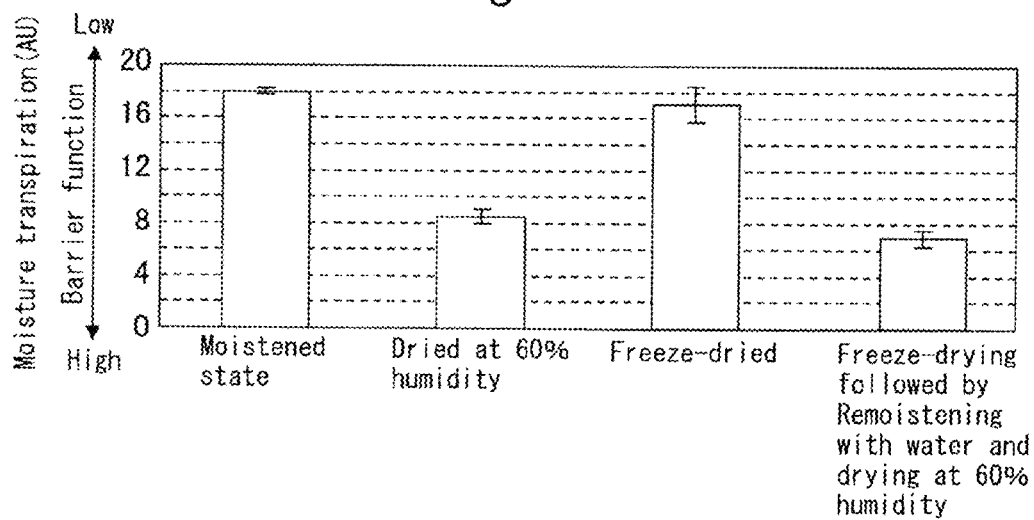
FIG. 5 is a graph showing improvement in skin barrier function when the stratum corneum roughened by freeze-drying is remoistened with water.
Figure 6:
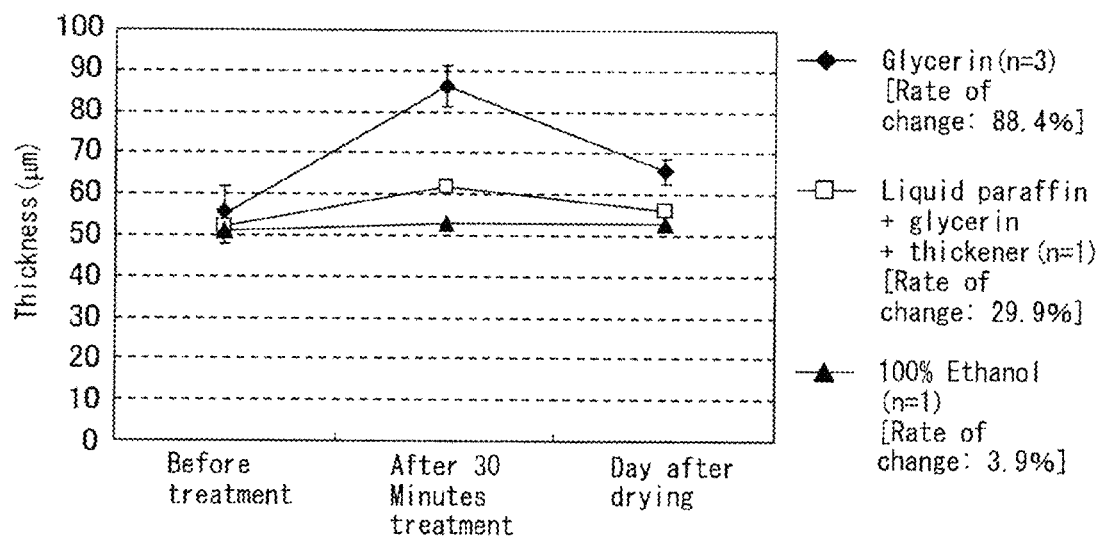
FIG. 6 is a graph showing change in thickness of a stratum corneum sheet when the stratum corneum sheet has been wetted with a liquid. The thickness increased when moistened with a 10% glycerin aqueous solution and a liquid paraffin+glycerin+thickener aqueous solution, and then decreased after drying, while there was no change in thickness when moistened with 100% ethanol.

Example 4: Evaluation of Effect of Water Moistening on Stratum Corneum Transparency Using the method for measuring stratum corneum transparency in Example 1, the stratum corneum transparency was measured with the following samples: a stratum corneum sheet moistened with water, a stratum corneum sheet moistened with water and then dried for 18 hours under conditions of 34 degrees, 60% humidity using a thermostatic bath (MTH-2200, Sanyo Electric, Tokyo, Japan), a stratum corneum sheet moistened with water, frozen at −20 degrees with a freeze-drying apparatus (VD-80, product of Taitec) and then freeze-dried for 2 hours with the same apparatus, and a stratum corneum sheet moistened with water and then subjected to the same freeze-drying, followed by re-moistening with water and then drying for 18 hours under conditions of 60% humidity (FIG. 4). The water moistening and water re-moistening was carried out by placement in water for 18 hours.

Example 5: Evaluation of Effect of Water Moistening on Stratum Corneum Skin Barrier Function Using the method for measuring skin barrier function in Example 2, the stratum corneum transparency was measured with the following samples: a stratum corneum sheet moistened with water, a stratum corneum sheet moistened with water and then dried for 18 hours under conditions of 34° C., 60% humidity, a stratum corneum sheet moistened with water, frozen to −20° C. with a freeze-drying apparatus (VD-80, product of Taitec) and then freeze-dried for 2 hours with the same apparatus, and a stratum corneum sheet moistened with water and then subjected to freeze-drying in the same manner, re-moistened with water and then dried under conditions of 34° C., 60% humidity. The water moistening and water re-moistening was carried out by placing it in water for 18 hours.

Judging from the experiments of Examples 4 and 5, water remoistening and drying of the stratum corneum damaged by freeze-drying restored both the transparency and skin barrier function of the stratum corneum to the same degree as the state dried at 60% humidity instead of freeze-drying, indicating that water moistening and drying improves the condition of skin.

Example 6: Evaluation of Reagents for their Ameliorating Effects on Skin Based on Change in Stratum Corneum Thickness The thickness of a J-TEC Human Reconstituted Epidermis Model (stratum corneum sheet) before the experiment was measured with a caliper (Caliper No. 227-201 by Mitsutoyo Corp.) (one location each) (A). The stratum corneum sheet was further wetted for 30 minutes in a 10% glycerin aqueous solution, an aqueous solution of liquid paraffin (10%), glycerin (10%), POE(60) hydrogenated castor oil (10%), carboxyvinyl polymer (product name: CARBOPOL 981, Lubrizol Advanced Materials, Inc.) (0.2%) and KOH (0.1%) (liquid paraffin+glycerin+thickener aqueous solution), and in 100% ethanol, and immediately upon completion of wetting, the thickness of the stratum corneum sheet was measured with a caliper in the same manner (B).

It was further dried for 18 hours under conditions of 34° C., 60% humidity and the stratum corneum sheet was measured (C). Using theses results, the thickness change rate (%) of the stratum corneum sheet was measured based on the following formula 1:

$$\text{Thickness change rate (\%)} = (B-A) \times 100/A - (C-B) \times 100/C$$

After subsequent drying, the transparency of the stratum corneum sheet was visually examined. The results for thickness change and transparency of the stratum corneum sheet are shown in Table 1.

TABLE 1

| Sample | Thickness change rate (%) | Transparency |
|---|---|---|
| 10% Glycerin solution | 88.4 | Good |
| Liquid paraffin + glycerin + thickener solution | 29.9 | Good |
| 100% Ethanol | 3.9 | Poor |

Figure 7:
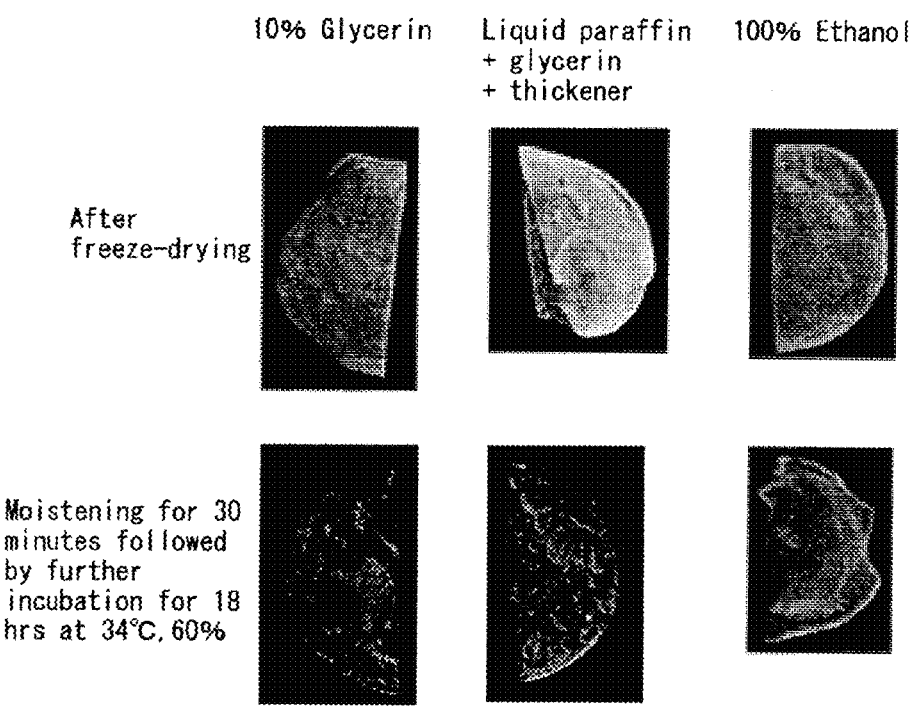
FIG. 7 shows the transparency and stratum corneum transmittance effects when a freeze-dried stratum corneum sheet has been moistened with liquid and then dried. The transparency was high and the stratum corneum layer transmittance was high when moistened with a 10% glycerin aqueous solution and a liquid paraffin+glycerin+thickener aqueous solution, while the transparency was low and the stratum corneum transmittance was also low when moistened with 100% ethanol.
Figure 7:
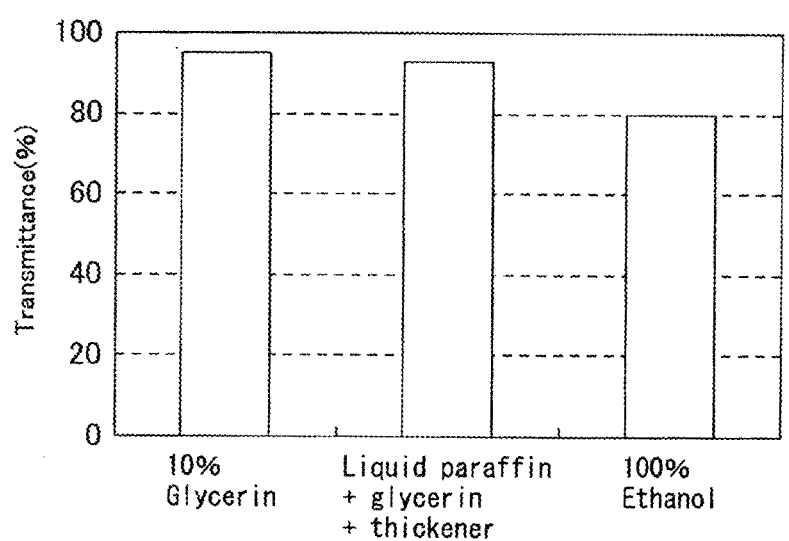

Next, a J-TEC Human Reconstituted Epidermis model (stratum corneum sheet) was subjected to freeze-drying to obtain a white opaque stratum corneum sheet. The freeze-dried stratum corneum sheet was wetted for 30 minutes in a 10% glycerin aqueous solution, in an aqueous solution of liquid paraffin (10%), glycerin (10%), POE(60) hydrogenated castor oil (10%), carboxyvinyl polymer (product name: CARBOPOL 981 by Lubrizol Advanced Materials, Inc.) (0.2%) and KOH (0.1%) (liquid paraffin+glycerin+thickener aqueous solution), and in 100% ethanol, and after removing the liquid, drying was performed for 18 hours in an atmosphere at 34° C., 60% humidity, and the sheet was photographed (FIG. 7).

A stratum corneum with high transparency was obtained when wetting was in the 10% glycerin aqueous solution or liquid paraffin+glycerin+thickener aqueous solution, but a stratum corneum with still low transparency was obtained when wetting was with liquid paraffin. The transmittance was measured using an HR100 spectrophotometer by Murakami Color Research Laboratory Co., Ltd. Comparison with Table 1 showed that stratum corneum with high transparency is obtained when the stratum corneum thickness change is at least 20%. Since higher transparency of the stratum corneum can be considered a more excellent skin condition, the state of improvement in skin can be evaluated based on the thickness change in the stratum corneum cells or cell layer from moistening in a liquid until drying.

Figure 8:
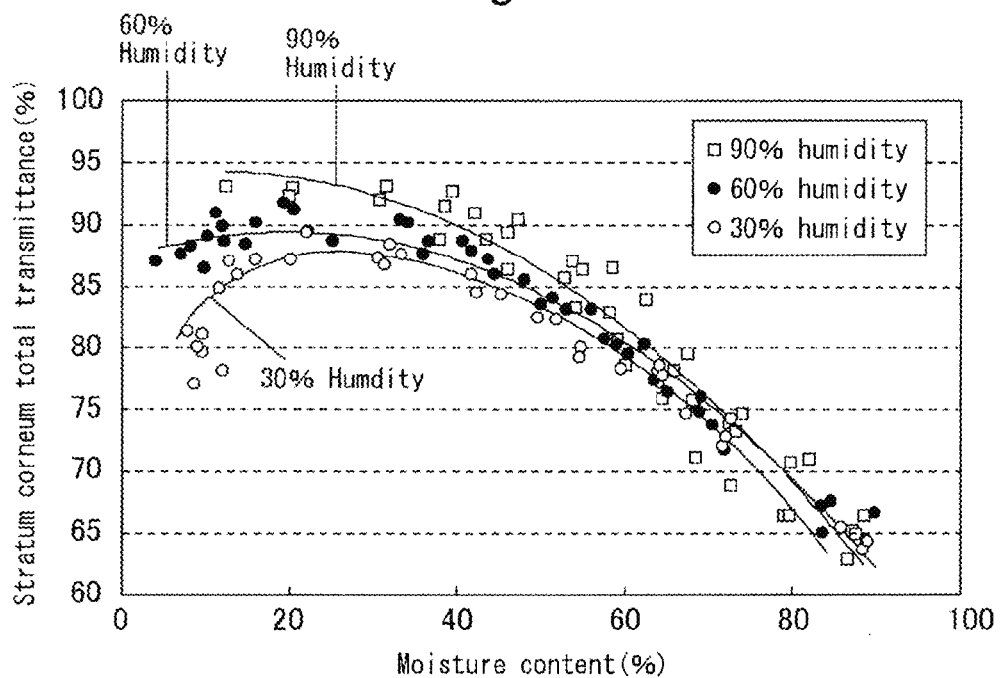
FIG. 8 is a graph showing the relationship between moisture content and stratum corneum total transmittance, after drying under conditions with 30% humidity, 60% humidity and 90% humidity.

Example 7: Change in Transparency of Stratum Corneum Based on Humidity in Drying Step The drying step in the experiment of Example 1 was conducted at a 30% and 60% humidity and at 90% humidity, to plot stratum corneum total transmittance against moisture content (%) (FIG. 8). FIG. 8 shows that drying at high humidity results in greater improvement in stratum corneum transparency. This experiment supports the use of a method for evaluating cosmetics that are suitable for given environments. In other words, when stratum corneum transmittance (%) is plotted against moisture content (%) obtained in the step of drying a test cosmetic at a prescribed humidity and temperature, and a plot diagram is drawn and a fitted curve obtained, the cosmetic is evaluated to be suitable for improving stratum corneum transparency if the fitted curve is included within the region between a fitted curve (1) obtained in the step of applying water to the stratum corneum and drying under conditions of the aforementioned prescribed temperature and at least 30% and less than 90% humidity, and a fitted curve (2) obtained in the step of drying under conditions with the aforementioned prescribed temperature and 90% humidity. It may be evaluated as an even more suitable cosmetic when the lower limit for the humidity under the conditions in which the fitted curve (1) is obtained, is a lower limit selected from the group consisting of 60%, 70% and 80%.

Figure 9:
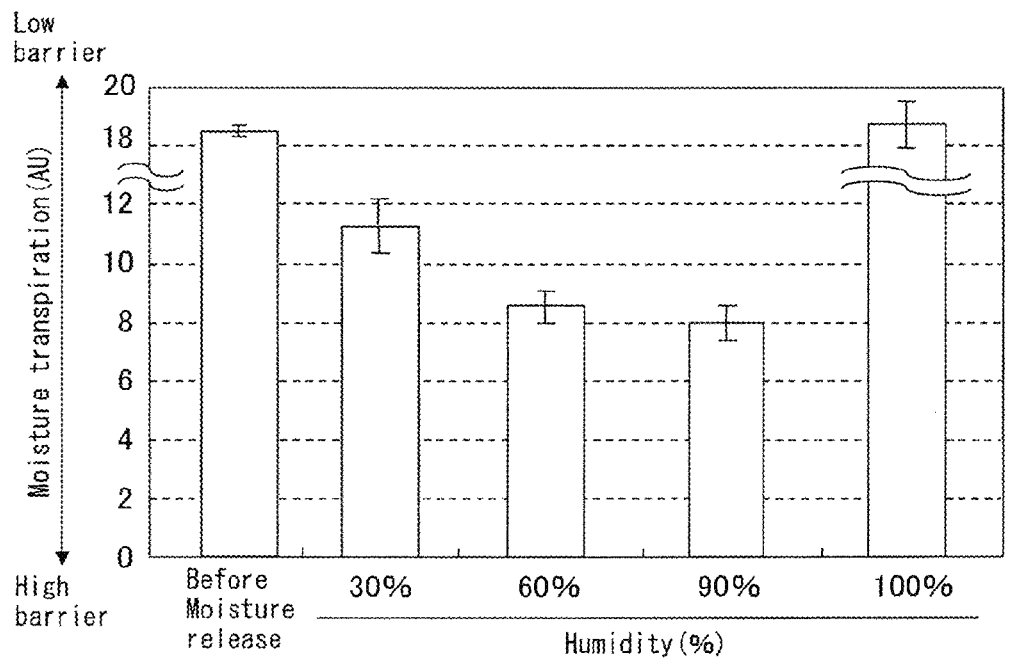
FIG. 9 is a graph showing skin barrier function, after drying under conditions with 30% humidity, 60% humidity and 90% humidity.

Example 8: Change in Skin Barrier Function of Stratum Corneum Based on Humidity in Drying Step The drying step in the experiment of Example 2 was conducted at humidities of 30%, 60% and 90%, and the moisture transpiration was measured (FIG. 9). This graph shows that the skin barrier function of the stratum corneum is improved when drying is carried out at high humidity, whereas the effect on skin barrier function was low when drying was at 60% or at 90% humidity.

The invention claimed is:

1. A method for evaluating a cosmetic for improving skin transparency and skin barrier function comprising:
    (a) measuring a thickness of cells or a cell layer of stratum corneum selected from the group consisting of an isolated stratum corneum and a cultured stratum corneum in a dry state before application of the cosmetic to determine a value A,
    (b) applying the cosmetic to the stratum corneum,
    (c) measuring said thickness after application of the cosmetic taken when the stratum corneum is in a moist state to determine a value B,
    (d) drying the stratum corneum,
    (e) measuring said thickness after application of the cosmetic taken when the stratum corneum is in a dry state to determine a value C,
    (f) measuring a change in thickness of a stratum corneum brought about by applying the cosmetic, wherein the change in thickness of stratum corneum is calculated according to the formula:

the change in thickness of stratum corneum=$(B-A)\times 100/A - (C-B)\times 100/C$, and wherein the change in thickness of stratum corneum from step (f) can determine whether the cosmetic results in an improvement in skin transparency and skin barrier function, wherein a higher change in thickness of stratum corneum corresponds to improvement in skin transparency and skin barrier function.

2. The method of claim 1, wherein a cosmetic is selected that provides a change in the thickness of the stratum corneum between 20% to 150%.

3. The method of claim 1, wherein a cosmetic is selected that provides a change in the thickness of the stratum corneum between 25% to 100%.

* * * * *